(12) United States Patent
Hochberg

(10) Patent No.: US 8,747,346 B2
(45) Date of Patent: Jun. 10, 2014

(54) HEMOSTATIC AGENT APPLICATOR FOR SURVICAL PROCEDURES

(76) Inventor: Martin Hochberg, Boynton Beach, FL (US)

( * ) Notice: Subject to any disclaimer, the term of this patent is extended or adjusted under 35 U.S.C. 154(b) by 783 days.

(21) Appl. No.: 12/131,056

(22) Filed: May 31, 2008

(65) Prior Publication Data

US 2009/0182259 A1  Jul. 16, 2009

Related U.S. Application Data

(60) Provisional application No. 60/932,590, filed on Jun. 1, 2007.

(51) Int. Cl.
*A61F 13/20* (2006.01)

(52) U.S. Cl.
USPC .............................................. 604/15; 604/14

(58) Field of Classification Search
USPC ...................................................... 604/11–18
See application file for complete search history.

(56) References Cited

U.S. PATENT DOCUMENTS

| | | | | |
|---|---|---|---|---|
| 4,413,986 | A * | 11/1983 | Jacobs | 604/14 |
| 6,416,779 | B1 * | 7/2002 | D'Augustine et al. | 424/430 |
| 6,526,980 | B1 * | 3/2003 | Tracy et al. | 128/830 |
| 7,344,732 | B2 * | 3/2008 | Gehling | 424/431 |
| 7,527,614 | B2 * | 5/2009 | Heuer et al. | 604/385.18 |
| 7,666,160 | B2 * | 2/2010 | Rajala et al. | 604/13 |
| 7,708,726 | B2 * | 5/2010 | Hayes et al. | 604/385.17 |

* cited by examiner

*Primary Examiner* — Lynne Anderson
(74) *Attorney, Agent, or Firm* — Joseph Beckman

(57) ABSTRACT

An apparatus for applying agents, including hemostatic agent, to the cervix and accompanying areas.

8 Claims, 4 Drawing Sheets

HEMOSTATIC AGENT APPLICATOR FOR SURVICAL PROCEDURES

STATEMENT OF PRIORITY

This application is a Non-Provisional Application which claims the benefit of U.S. Provisional Application Ser. No. 60/932,590, filed Jun. 1, 2007, the disclosures of which are incorporated herein by reference.

FIELD OF THE INVENTION

This invention relates to an apparatus for applying agents, including a hemostatic agent, to the cervix and accompanying areas.

SUMMARY OF THE INVENTION

An object of the present invention is to provide an applicator for applying a hemostatic agent to the cervix subsequent to biopsy or other surgical procedures.

A further object of the present invention is to provide a means to secure the hemostatic agent to the cervix in an efficient manner to stop blood flow without the need to unduly manipulate the applicator or hold the applicator with agent in place to secure the agent against the cervix.

Other objects and advantages of the invention will be apparent from the following description, the accompanying drawings and the appended claims.

DETAILED DESCRIPTION OF THE INVENTION

Figure 1:
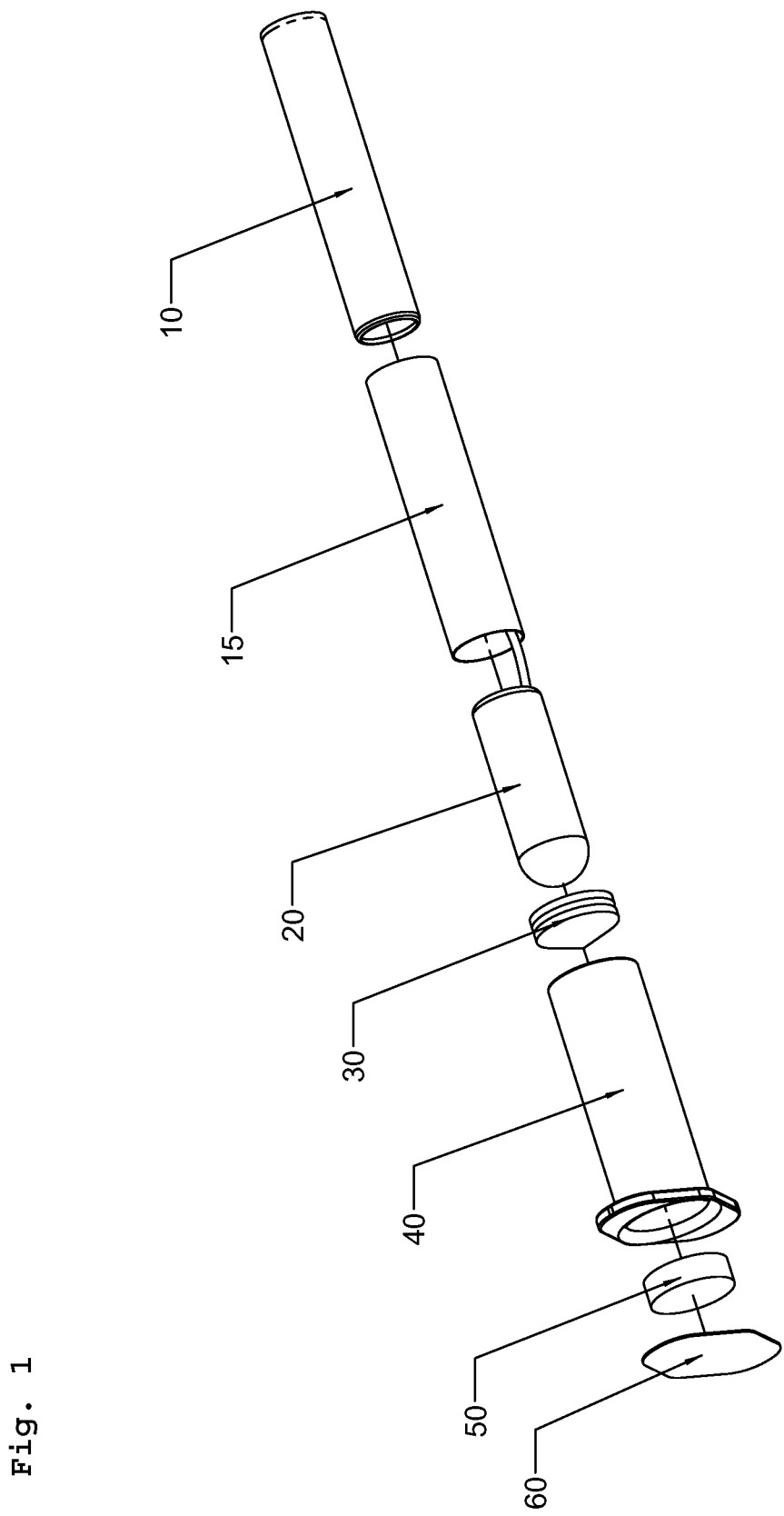
FIG. 1 depicts an exploded view of an embodiment of the present invention.
Figure 4:
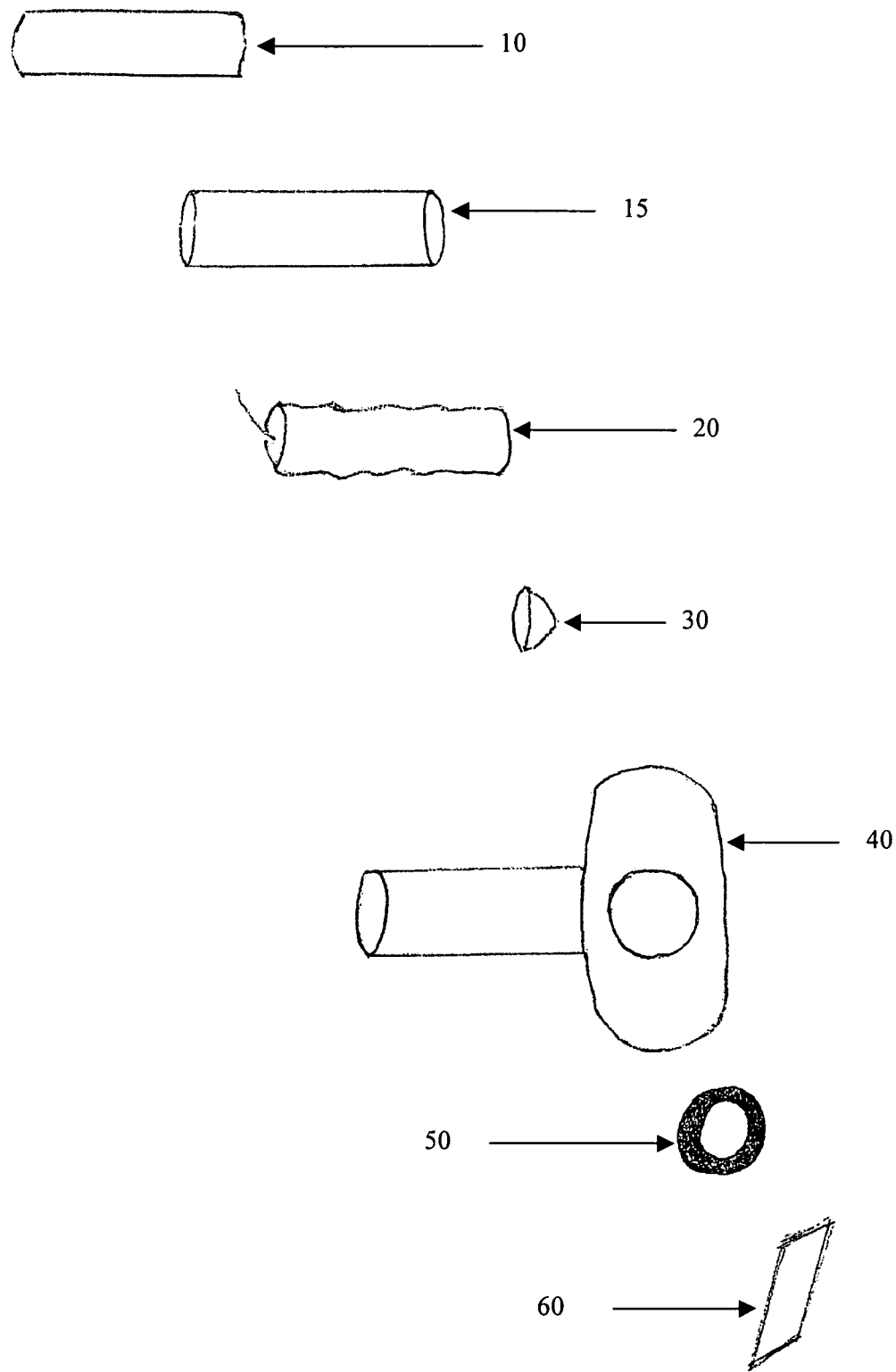
FIG. 4 depicts an alternative exploded view of an embodiment of the present invention.

FIG. 1 depicts an exploded view of an embodiment of the invention. A tampon plunger (10) sits atop a tampon (20) or its equivalent and a plunger disc (30) attached to the tampon (20), all of which is substantially situated within an application cylinder (40) including a flange. In an alternative embodiment, the tampon may additionally be contained within a tampon casing (15), as reflected in FIG. 4, which is then fitted within the hollow application cylinder (40). The tampon plunger is sized so as to fit within the application cylinder or the tampon casing, if present, so as to be able to direct the tampon through the flange end of the application cylinder with an appropriate application of force. A liquid, solid or semi-solid agent is placed upon the plunger disc surface which sits within the application cylinder and below the flange surface. The device is sealed at the flange opening until ready for use by means of a foil seal, tape or other equivalent sealing means which is readily removable for application of the agent. The flange is preferably sized and shaped for secure placement and maximum contact with the cervix.

In use, the seal is removed, exposing the agent, which may be any number of medicinal liquids, solids or semi-solids. One popular agent is Monsel's solution, gel or paste, which is a hemostatic agent commonly utilized to stop bleeding in the cervix area consequent to a surgical procedure. The Application Cylinder is held in one hand and inserted flange-first into the vaginal canal until the flange is secured against the cervix surface. The tampon plunger is then utilized to push the tampon and plunger disc securely against the cervix surface, thereby securing the agent to the cervix. The Application Cylinder is then removed, leaving the tampon and plunger disc combination in place within the vaginal canal. The agent is periodically secured against the cervix, performing a hemostatic or other function, until removal of the tampon and plunger disc combination.

Figure 2:
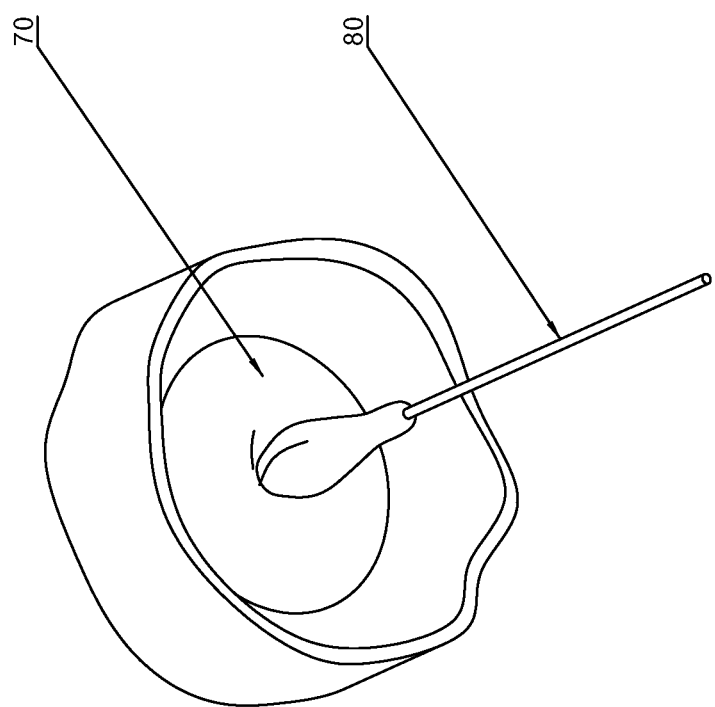
FIG. 2 shows the prior art application of an agent to a cervix via cotton tipped dispenser.

FIG. 2 depicts prior art application of agents to the cervix surface (70) via mean of a cotton tipped instrument or its equivalent (80). Post-surgical application of a hemostatic agent, particularly a liquid or semi-solid (gel, paste or equivalent), via means of a cotton tipped instrument or its equivalent has not been an effective means of securing the agent to the cervix surface for a sufficient time to enable effective hemostatic treatment. Very often, the physician or assistant is required to hold the prior art applicator with agent against the cervix until bleeding is controlled. This is inefficient and uncomfortable for both the physician and the patient.

Figure 3:
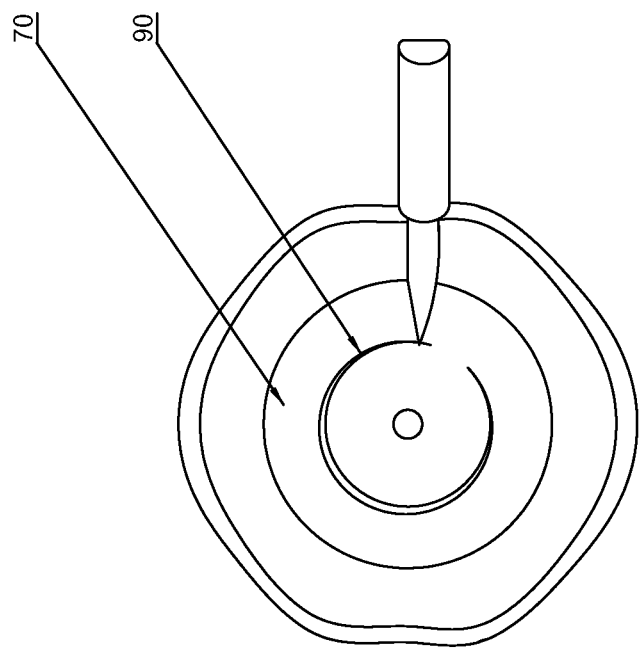
FIG. 3 indicates the cervix area to which agents are applied during and post surgical procedure.

FIG. 3 depicts a cervix (70) and a circular area indicated by a dotted arrow (90) indicating a common area of surgical procedure requiring the application of an agent. The flange of the Applicator Cylinder would be placed around this area and the plunger disc would deliver the agent to this area, being held in place by the tampon, without further effort by the physician.

Although preferred embodiments of the system and apparatus of the present invention have been illustrated in the accompanying Drawings and described in the foregoing Detailed Description, it will be understood that the invention is not limited to the embodiments disclosed, but is capable of numerous rearrangements, modifications and substitutions without departing from the spirit of the invention as set forth and defined by the following claims.

What is claimed is:

1. An apparatus for applying liquid, solid or semi-solid agents to a cervix, the apparatus comprising:
    an applicator cylinder having a first end and a second end, the first end including a flange and the second end accepting within the cylinder a tampon plunger, tampon material and a plunger disc with a convex shaped outer surface facing away from the tampon material for contacting an agent, wherein the tampon plunger may apply force against the tampon material and plunger disc, which force may then direct and maintain the agent against the cervix surface.

2. The apparatus of claim 1 further comprising a liquid, solid or semi-solid agent contained on the plunger disc and within the applicator cylinder for application to a cervix.

3. The apparatus of claim 2 further comprising a seal to contain the agent against the plunger disc until ready for application.

4. The apparatus of claim 1 wherein the plunger disc is formed integral with the tampon material.

5. The apparatus of claim 1 further comprising a tampon casing.

6. An apparatus for applying liquid, solid or semi-solid agents to a cervix, the apparatus comprising:
    an applicator cylinder having a first end and a second end, the first end including a flange and the second end accepting within the cylinder a plunger, tampon material and a plunger disc generally convex in shape at an end contacting a cervix and facing away from the tampon material, wherein the plunger may apply force against the tampon material and plunger disc, which force may then direct the agent against the cervix surface.

7. A method of applying liquid, solid or semi-solid agents to a cervix, the method comprising the steps of:

Applying an agent to a convex shaped outer surface of a conical plunger disc;

Inserting the convex shaped outer surface of the conical plunger disc containing the agent into the vaginal canal such that the agent makes contact with the cervix; and Maintaining contact between the cervix and the agent by means of a tampon.

8. The method of claim 7 further comprising the step of attaching the outwardly conical plunger disc to the tampon prior to insertion into the vaginal canal.

* * * * *

UNITED STATES PATENT AND TRADEMARK OFFICE
CERTIFICATE OF CORRECTION

PATENT NO. : 8,747,346 B2  Page 1 of 1
APPLICATION NO. : 12/131056
DATED : June 10, 2014
INVENTOR(S) : Martin N. Hochberg It is certified that error appears in the above-identified patent and that said Letters Patent is hereby corrected as shown below:

On the Title Page, Item (54), and in the Specification, Column 1, line 2, the title: Hemostatic Agent... has the word "Survical" which should have been
"CERVICAL".

Signed and Sealed this
Twenty-third Day of September, 2014

Michelle K. Lee
*Deputy Director of the United States Patent and Trademark Office*